United States Patent
Yamamoto et al.

(10) Patent No.: US 10,617,393 B2
(45) Date of Patent: Apr. 14, 2020

(54) ULTRASONIC DIAGNOSTIC DEVICE AND ULTRASONIC IMAGE GENERATION METHOD

(71) Applicant: FUJIFILM Corporation, Tokyo (JP)

(72) Inventors: Hiroaki Yamamoto, Ashigara-kami-gun (JP); Shoji Hara, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 538 days.

(21) Appl. No.: 15/013,571

(22) Filed: Feb. 2, 2016

(65) Prior Publication Data
US 2016/0206289 A1    Jul. 21, 2016

Related U.S. Application Data

(63) Continuation of application No. PCT/JP2014/060963, filed on Apr. 17, 2014.

(30) Foreign Application Priority Data

Aug. 27, 2013   (JP) .................................. 2013-175711

(51) Int. Cl.
| | | |
|---|---|---|
| *A61B 8/08* | (2006.01) | |
| *A61B 8/00* | (2006.01) | |
| *G01S 15/89* | (2006.01) | |
| *G01S 7/52* | (2006.01) | |

(Continued)

(52) U.S. Cl.
CPC .......... *A61B 8/5207* (2013.01); *A61B 8/0841* (2013.01); *A61B 8/145* (2013.01);
(Continued)

(58) Field of Classification Search
CPC ................. G01S 15/8915; A61B 8/463; A61B 2017/3413; A61B 8/0841; A61B 8/145;
(Continued)

(56) References Cited

U.S. PATENT DOCUMENTS

| 9,832,452 B1 * | 11/2017 | Fotland .................. H04N 13/20 |
| 2002/0173719 A1 * | 11/2002 | Zhao ..................... A61B 8/0833 |
| | | 600/437 |

(Continued)

FOREIGN PATENT DOCUMENTS

| JP | 2012-192162 A | 10/2012 |
| JP | 2012-213606 A | 11/2012 |

OTHER PUBLICATIONS

Powers et. al., "Medical Ultrasound System", Interface Focus (2011) 1, 477-489.*

(Continued)

*Primary Examiner* — Katherine L Fernandez
*Assistant Examiner* — Yi-Shan Yang
(74) *Attorney, Agent, or Firm* — Birch, Stewart, Kolasch & Birch, LLP.

(57) ABSTRACT

An ultrasonic diagnostic device includes: a probe including a plurality of elements; a transmission unit that transmits an ultrasonic beam by performing transmission focusing in a first direction from the plurality of elements; a reception unit that generates element data by processing reception signals output from the plurality of elements that has received an ultrasonic echo generated by the transmitted ultrasonic beam; an element data processing unit that generates reflection component removal data by removing a reflection component generated from the first direction from the element data; an image generation unit that generates an ultrasonic image by performing reception focusing for the element data; and a control unit that controls the image generation unit to generate an image signal along a second direction different from the first direction by performing reception focusing in the second direction for the reflection component removal data generated by the element data processing unit.

7 Claims, 9 Drawing Sheets

(51) Int. Cl.
  *A61B 8/14* (2006.01)
  *A61B 17/34* (2006.01)
  *G10K 11/34* (2006.01)
(52) U.S. Cl.
  CPC .......... *A61B 8/4488* (2013.01); *A61B 8/5238* (2013.01); *A61B 8/5269* (2013.01); *G01S 7/52046* (2013.01); *G01S 15/8915* (2013.01); *A61B 8/463* (2013.01); *A61B 2017/3413* (2013.01); *G01S 7/5209* (2013.01); *G01S 7/52074* (2013.01); *G10K 11/346* (2013.01)
(58) Field of Classification Search
  CPC ... A61B 8/4488; A61B 8/5207; A61B 8/5238; A61B 8/5269
  See application file for complete search history.

(56) References Cited

U.S. PATENT DOCUMENTS

| | | | |
|---|---|---|---|
| 2010/0056917 A1* | 3/2010 | Karasawa | A61B 8/0833 600/443 |
| 2012/0134233 A1* | 5/2012 | Lin | G01S 7/52022 367/7 |
| 2012/0226164 A1 | 9/2012 | Tashiro et al. | |
| 2012/0253181 A1 | 10/2012 | Okamura et al. | |
| 2015/0055821 A1* | 2/2015 | Fotland | G06K 9/3241 382/103 |
| 2015/0223776 A1* | 8/2015 | Ohuchi | A61B 8/0841 600/424 |

OTHER PUBLICATIONS

Japanese Office Action dated Aug. 9, 2016, for Japanese Application No. 2013-175711 with the English translation.
International Search Report for PCT/JP2014/060963 dated Jun. 10, 2014.
English translation of the International Preliminary Report on Patentability and Written Opinion of the International Searching Authority (Forms PCT/IB/338, PCT/IB/373 and PCT/ISA/237), dated Mar. 10, 2016, for International Application No. PCT/JP2014/060963.

* cited by examiner

FIRST ELEMENT DATA

SECOND ELEMENT DATA

REFLECTION COMPONENT REMOVAL DATA

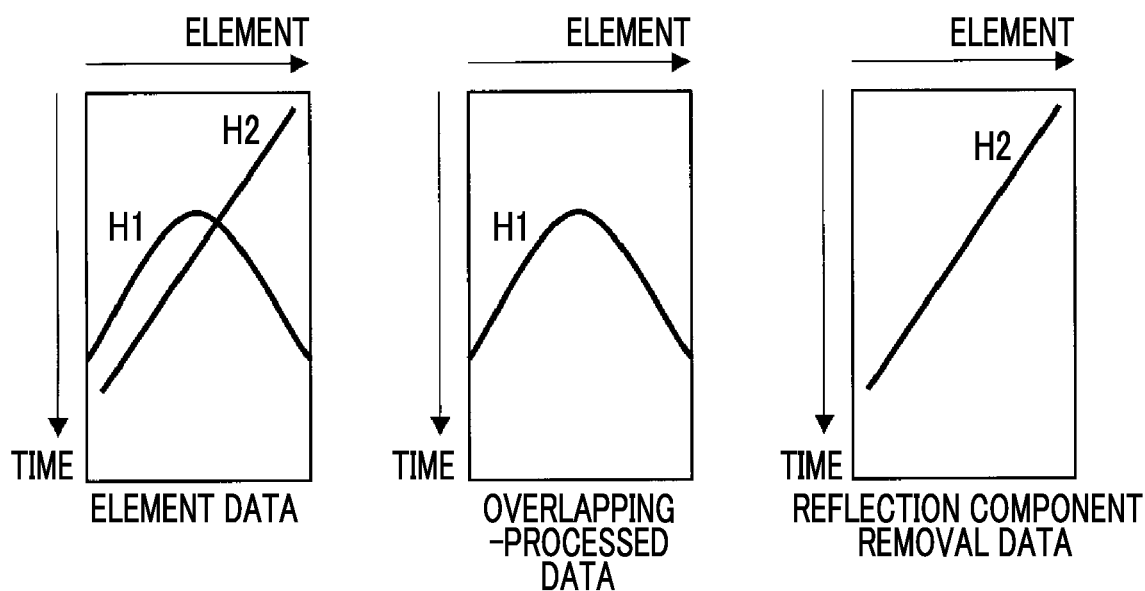

ELEMENT DATA

SIMULATION DATA

REFLECTION COMPONENT REMOVAL DATA

ULTRASONIC DIAGNOSTIC DEVICE AND ULTRASONIC IMAGE GENERATION METHOD

CROSS-REFERENCE TO RELATED APPLICATIONS

This application is a Continuation of PCT International Application No. PCT/JP2014/060963 filed on Apr. 17, 2014, which claims priority under 35 U.S.C. § 119(a) to Japanese Patent Application No. 2013-175711 filed on Aug. 27, 2013. The above application is hereby expressly incorporated by reference, in its entirety, into the present application.

BACKGROUND OF THE INVENTION

1. Field of the Invention

The present invention relates to an ultrasonic diagnostic device and an ultrasonic image generation method, and in particular, to an ultrasonic diagnostic device and an ultrasonic image generation method for generating an ultrasonic image by performing reception focusing in a different direction from the transmission direction of an ultrasonic beam.

2. Description of the Related Art

Conventionally, in the medical field, an ultrasonic diagnostic device using an ultrasonic image has been put into practical use. In general, this kind of ultrasonic diagnostic device generates an ultrasonic image by transmitting an ultrasonic beam toward a subject from the ultrasonic probe, receiving an ultrasonic echo from the subject using the ultrasonic probe, and electrically processing the reception signal.

In such an ultrasonic diagnostic device, a tomographic image of the inside of the subject located immediately below the probe cannot be observed in real time. Accordingly, for example, when inserting the needle to the target location in the subject, an ultrasonic image of the inside of the subject is generated by placing the probe immediately above a target location and the needle is obliquely inserted toward the target location from the vicinity of the probe, so that the needle is inserted while checking the position of the needle in the subject on an ultrasonic image.

However, in general, the surface of the needle is smooth. Accordingly, an ultrasonic beam having propagated through the subject from the probe is likely to be regularly reflected on the surface of the needle. In addition, since the needle is obliquely inserted toward the target location, it may be difficult to visualize the needle by capturing the specular reflection of the ultrasonic beam transmitted in the normal direction of the probe in the reception opening of the probe.

Therefore, visualizing the needle by transmitting an ultrasonic beam in a direction perpendicular to the needle instead of the normal direction of the probe and performing reception focusing has been known.

For example, JP2012-213606A discloses an ultrasonic diagnostic device that generates a first image by transmitting and receiving an ultrasonic beam in a first direction perpendicular to the element surface of a probe for the purpose of tissue imaging, generates a second image group by transmitting and receiving an ultrasonic beam in a plurality of second directions, which are different from the direction perpendicular to the element surface, for the purpose of needle imaging, generates an image in which a needle is visualized by analyzing the second image group, and combines the image with the first image.

According to the device disclosed in JP2012-213606A, since a direction perpendicular to the needle is included in the plurality of second directions, it is possible to generate an ultrasonic image in which the needle is satisfactorily visualized.

SUMMARY OF THE INVENTION

In the device disclosed in JP2012-213606A, however, since the transmission of an ultrasonic beam in a first direction for tissue imaging and multiple transmissions of an ultrasonic beam in a second direction for needle imaging are required, there has been a problem that the frame rate is reduced.

Therefore, for example, a method of generating a tissue image by performing reception focusing in the normal direction of the probe for reception signals obtained by transmitting ultrasonic beams in the normal direction of the probe and generating a needle image by performing reception focusing in a direction perpendicular to the needle has been devised by the applicant. According to this method, it is possible to generate both a tissue image and a needle image with one transmission of ultrasonic beams.

However, since the ultrasonic beam is transmitted in the normal direction of the probe, both the strength of the ultrasonic wave transmitted in the direction of the needle from each element of the probe and the signal strength when each element receives the reflected wave from the needle are lower than the strength of the ultrasonic wave transmitted in the normal direction of the probe and the signal strength when the reflected wave is received from the normal direction. As a result, since the S/N ratio of the image is reduced, there is a possibility that it becomes difficult to visualize the needle clearly.

The present invention has been made in order to solve such a conventional problem, and it is an object of the present invention to provide an ultrasonic diagnostic device and an ultrasonic image generation method capable of generating a clear ultrasonic image even if reception focusing is performed in a different direction from the transmission direction of the ultrasonic beam.

An ultrasonic diagnostic device according to the present invention includes: a probe including a plurality of elements that are arranged; a transmission unit that transmits an ultrasonic beam by performing transmission focusing in a first direction from the plurality of elements of the probe; a reception unit that generates element data by processing reception signals output from the plurality of elements of the probe that has received an ultrasonic echo generated by the ultrasonic beam transmitted from the transmission unit; an element data processing unit that generates reflection component removal data by removing a reflection component generated from the first direction from the element data; an image generation unit that generates an ultrasonic image by performing reception focusing for the element data; and a control unit that controls the image generation unit to generate an image signal along a second direction different from the first direction by performing reception focusing in the second direction for the reflection component removal data generated by the element data processing unit.

The transmission unit can form at least two focuses at different positions in the first direction to sequentially transmit a plurality of ultrasonic beams, and the element data processing unit can be configured to generate the reflection component removal data from a plurality of pieces of element data generated by the reception unit corresponding to the plurality of ultrasonic beams.

In this case, the element data processing unit generates the reflection component removal data by taking a difference between the plurality of pieces of element data.

In addition, when taking a difference between the plurality of pieces of element data, the element data processing unit can take a difference after giving weighting to any one of the plurality of pieces of element data or to the plurality of pieces of element data.

The element data processing unit can be configured to generate overlapping-processed data in which a reflection component generated from the first direction is emphasized by overlapping a predetermined number of pieces of element data generated by the reception unit with each other by phase matching corresponding to the predetermined number of consecutive scanning lines and generate the reflection component removal data using the overlapping-processed data.

In this case, the element data processing unit generates the reflection component removal data by taking a difference between the element data by the plurality of elements generated by the reception unit and the overlapping-processed data.

When taking a difference between the element data by the plurality of elements generated by the reception unit and the overlapping-processed data, the element data processing unit can take a difference after giving weighting to either the element data by the plurality of elements generated by the reception unit or the overlapping-processed data or to both the element data by the plurality of elements generated by the reception unit and the overlapping-processed data.

The element data processing unit may be configured to generate simulation data indicating a reflected wave generated from the first direction by simulation and generate the reflection component removal data using the simulation data.

In this case, the element data processing unit generates the reflection component removal data by taking a difference between the element data by the plurality of elements generated by the reception unit and the simulation data.

When taking a difference between the element data by the plurality of elements generated by the reception unit and the simulation data, the element data processing unit can take a difference after giving weighting to either the element data by the plurality of elements generated by the reception unit or the simulation data or to both the element data by the plurality elements generated by the reception unit and the simulation data.

It is preferable that the image generation unit includes: a tissue image generation section that generates an image signal for tissue imaging along the first direction by performing reception focusing in the first direction for the element data; and a needle image generation section that generates an image signal for needle imaging along the second direction by performing reception focusing in the second direction for the reflection component removal data.

It is preferable to further include an image combination unit that combines the image signal for tissue imaging generated by the tissue image generation section and the image signal for needle imaging obtained by the needle image generation section. In addition, it is preferable to include a display unit that displays an image signal obtained by combination of the image combination unit.

In addition, it is also possible to include a display unit that displays an ultrasonic image generated by the image generation unit.

An ultrasonic image generation method according to the present invention includes: transmitting an ultrasonic beam by performing transmission focusing in a first direction from a plurality of elements of a probe; generating element data by processing reception signals output from the plurality of elements of the probe that has received an ultrasonic echo generated by the ultrasonic beam; generating reflection component removal data by removing a reflection component generated from the first direction from the element data; and generating an ultrasonic image along a second direction different from the first direction by performing reception focusing in the second direction for the reflection component removal data.

According to the present invention, element data is generated by transmitting an ultrasonic beam by performing transmission focusing in the first direction, reflection component removal data is generated by removing a reflection component generated from the first direction from the element data, and an ultrasonic image along the second direction different from the first direction is generated by performing reception focusing in the second direction for the reflection component removal data. Therefore, even if reception focusing is performed in a different direction from the transmission direction of the ultrasonic beam, it is possible to generate a clear ultrasonic image.

BRIEF DESCRIPTION OF THE DRAWINGS

FIGS. 8A-8C are diagrams schematically showing element data, overlapping-processed data, and reflection component removal data that are obtained in the second embodiment, respectively.

DESCRIPTION OF THE PREFERRED EMBODIMENTS

Hereinafter, embodiments of the present invention will be described with reference to the accompanying diagrams.

First Embodiment

Figure 1:
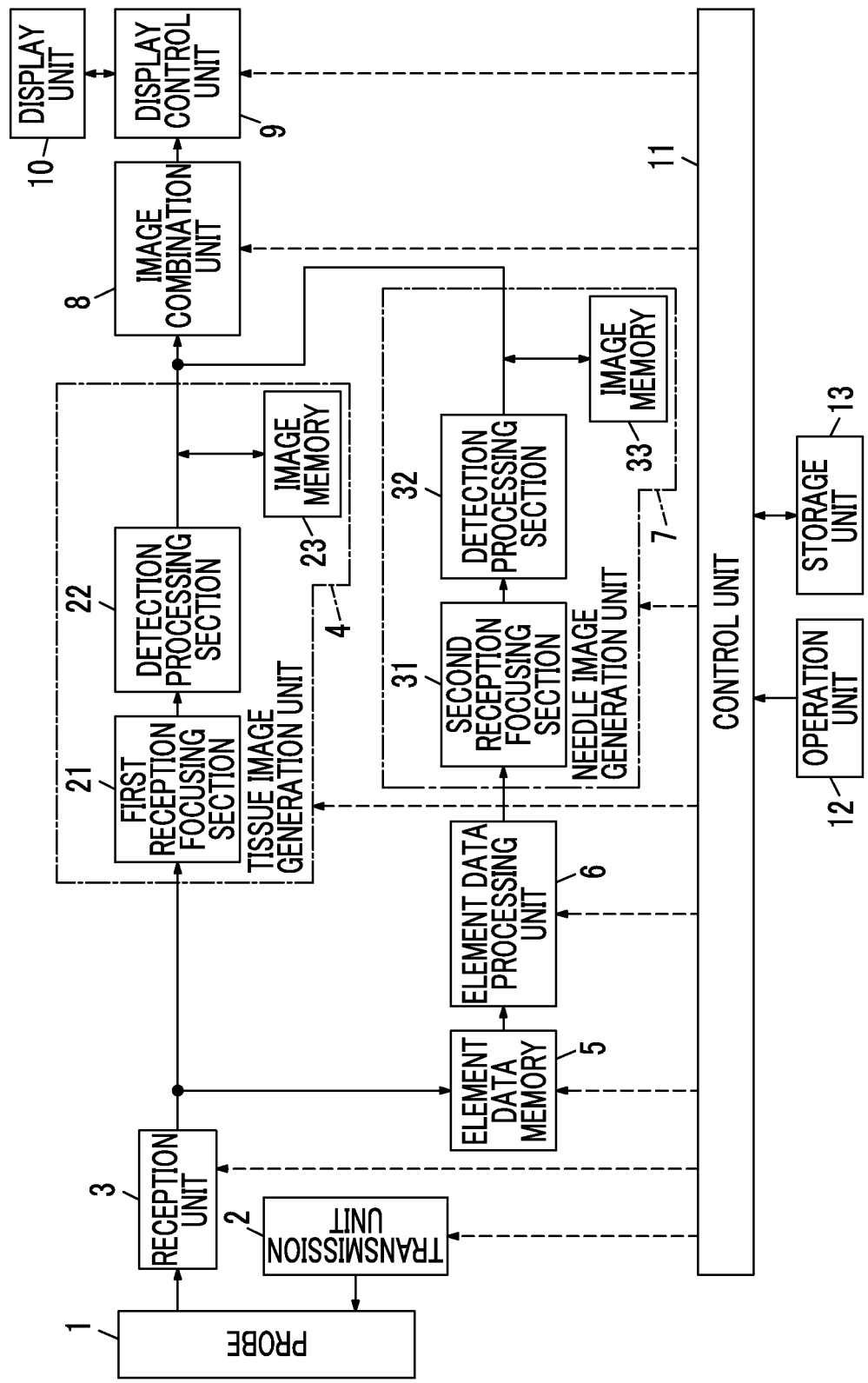
FIG. 1 is a block diagram showing the configuration of an ultrasonic diagnostic device according to a first embodiment of the present invention.

FIG. 1 shows the configuration of an ultrasonic diagnostic device according to a first embodiment of the present invention. The ultrasonic diagnostic device includes a probe 1, and a transmission unit 2 and a reception unit 3 are connected to the probe 1. A tissue image generation unit 4 and an element data memory 5 are connected in parallel to the reception unit 3, and a needle image generation unit 7 is connected to the element data memory 5 through an element data processing unit 6. An image combination unit 8 is connected to the tissue image generation unit 4 and the needle image generation unit 7, and a display unit 10 is connected to the image combination unit 8 through a display control unit 9.

The control unit 11 is connected to the transmission unit 2, the reception unit 3, the tissue image generation unit 4, the element data memory 5, the element data processing unit 6, the needle image generation unit 7, the image combination unit 8, and the display control unit 9. An operation unit 12 and a storage unit 13 are connected to the control unit 11.

The tissue image generation unit 4 serves to generate a tissue image of the subject, which is located immediately below the probe 1, and includes a first reception focusing section 21 connected to the reception unit 3 and a detection processing section 22 and an image memory 23 that are sequentially connected to the first reception focusing section 21. The detection processing section 22 and the image memory 23 are connected to the image combination unit 8.

On the other hand, the needle image generation unit 7 serves to generate an ultrasonic image of a needle inserted into the subject, and has the same configuration as the tissue image generation unit 4. That is, the needle image generation unit 7 includes a second reception focusing section 31 connected to the element data processing unit 6 and a detection processing section 32 and an image memory 33 that are sequentially connected to the second reception focusing section 31, and the detection processing section 32 and the image memory 33 are connected to the image combination unit 8.

The probe 1 includes a plurality of elements arranged in a one-dimensional or two-dimensional manner. Each of these elements is an ultrasonic transducer, and transmits an ultrasonic wave according to the driving signal supplied from the transmission unit 2, receives an ultrasonic echo from the subject, and outputs a reception signal. For example, each ultrasonic transducer is formed by a transducer in which electrodes are formed at both ends of the piezoelectric body formed of piezoelectric ceramic represented by lead zirconate titanate (PZT), a polymer piezoelectric element represented by polyvinylidene fluoride (PVDF), piezoelectric single crystal represented by lead magnesium niobate-lead titanate (PMN-PT), or the like, and has an ultrasonic wave transmitting and receiving surface with a predetermined area.

When a pulsed or continuous-wave voltage is applied to the electrodes of the transducer, the piezoelectric body expands and contracts to generate pulsed or continuous-wave ultrasonic waves from each transducer. By a combination of these ultrasonic waves, an ultrasonic beam is formed. In addition, the respective transducers expand and contract by receiving the propagating ultrasonic waves, thereby generating electrical signals. These electrical signals are output as reception signals of the ultrasonic waves.

The transmission unit 2 includes a plurality of pulse generators, for example. Based on a transmission delay pattern selected according to the control signal from the control unit 11, the transmission unit 2 adjusts the amount of delay of each driving signal so that ultrasonic waves emitted from the plurality of elements of the probe 1 form an ultrasonic beam to be transmitted in a first direction, and supplies the adjusted signals to the plurality of elements. Here, the first direction is set to the normal direction of the element surface of the probe 1.

The reception unit 3 generates digitized element data by amplifying the reception signal output from each element of the probe 1 and performing A/D conversion.

The first reception focusing section 21 of the tissue image generation unit 4 performs reception focusing in the first direction, that is, in the normal direction of the element surface of the probe 1 by generating delay correction data by performing delay correction for the element data generated by the reception unit 3 and adding up the pieces of delay correction data. Through the reception focusing processing, a sound ray signal for tissue imaging with narrowed focus of the ultrasonic echo is generated.

The detection processing section 22 generates a B-mode image signal for tissue imaging by correcting the attenuation due to the distance according to the depth of the reflection position of the ultrasonic wave for the sound ray signal generated by the first reception focusing section 21 and then performing envelope detection processing, and outputs the B-mode image signal to the image combination unit 8 or stores the B-mode image signal in the image memory 23.

The element data memory 5 stores the element data generated by the reception unit 3, and outputs the element data to the element data processing unit 6.

Figure 2:
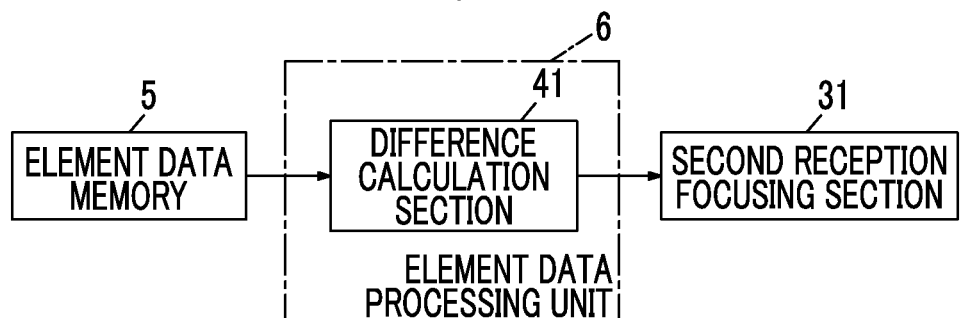
FIG. 2 is a diagram showing the configuration of an element data processing unit in the first embodiment.

The element data processing unit 6 generates reflection component removal data by removing reflection components, which are generated from the normal direction of the element surface of the probe 1 that is the first direction, from the element data generated by the reception unit 3. In the first embodiment, as shown in FIG. 2, the element data processing unit 6 is formed by a difference calculation section 41 connected to the element data memory 5.

The second reception focusing section 31 of the needle image generation unit 7 performs reception focusing in a second direction, which is different from the first direction, by generating delay correction data by performing delay correction for the reflection component removal data generated by the element data processing unit 6 and adding up the pieces of delay correction data. Here, the second direction is set to a direction perpendicular to the needle inserted into the body of the subject. Through the reception focusing processing, a sound ray signal for needle imaging with narrowed focus of the ultrasonic echo is generated.

The detection processing section 32 generates a B-mode image signal for needle imaging by correcting the attenuation due to the distance according to the depth of the reflection position of the ultrasonic wave for the sound ray signal generated by the second reception focusing section 31 and then performing envelope detection processing, and outputs the B-mode image signal to the image combination unit 8 or stores the B-mode image signal in the image memory 33.

The image combination unit 8 converts (raster conversion) the B-mode image signal for tissue imaging output from the tissue image generation unit 4 and the B-mode image signal for needle imaging output from the needle image generation unit 5 into image signals according to the normal television signal scanning method and performs various kinds of required image processing, such as gradation processing, and then combines the B-mode image signal for tissue imaging and the B-mode image signal for needle imaging. The display control unit 9 displays an ultrasonic image on the display unit 10 based on the B-mode image signal combined by the image combination unit 8.

The display unit 10 includes, for example, a display device, such as an LCD, and displays an ultrasonic image under the control of the display control unit 9.

The control unit 11 controls each unit of the ultrasonic diagnostic device based on the instruction input from the operating unit 12 by the operator.

The operation unit 12 is used when the operator performs an input operation, and can be formed by a keyboard, a mouse, a trackball, a touch panel, and the like.

The storage unit 13 stores an operation program and the like, and recording media, such as a hard disk, a flexible disk, an MO, an MT, a RAM, a CD-ROM, a DVD-ROM, an SD card, a CF card, and a USB memory, or a server may be used.

The element data processing unit 6, the first reception focusing section 21 and the detection processing section 22 of the tissue image generation unit 4, the second reception focusing section 31 and the detection processing section 32 of the needle image generation unit 7, the image combination unit 8, and the display control unit 9 are formed by using a CPU and an operation program causing the CPU to execute various kinds of processing. However, these may be formed by using digital circuits.

Figure 3:
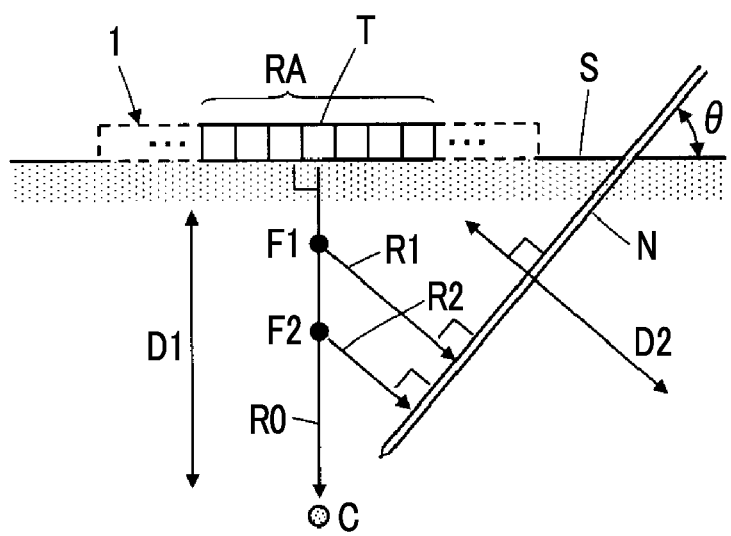
FIG. 3 is a diagram showing a state of transmission of the ultrasonic wave in the first embodiment.

A method of transmitting and receiving an ultrasonic wave in the first embodiment will be described. As shown in FIG. 3, it is assumed that a needle N is inserted at an angle θ from the vicinity of the probe 1 in a state in which the probe 1 is in contact with the body surface of a subject S.

First, a first transmission focus F1 is formed at a predetermined depth in the first direction D1 that is the normal direction of the element surface of the probe 1, and a first ultrasonic beam is transmitted toward the first direction D1 by the transmission unit 2. Then, the first ultrasonic beam propagates through the subject S with a predetermined spread after converging on the first transmission focus F1.

In this case, a transmission wave toward a reflection point C present in the first direction D1 through the first transmission focus F1 from the probe 1 propagates along a path R0 parallel to the first direction D1, and a reflected wave from the reflection point C is received by each element of the probe 1. In addition, a transmission wave traveling in the second direction D2 perpendicular to the needle N through the first transmission focus F1 from the probe 1 propagates along a path R1, and a reflected wave from the surface of the needle N is received by each element of the probe 1.

Then, a second transmission focus F2 is formed at a position, which is in the first direction D1 and is deeper than the first transmission focus F1, and a second ultrasonic beam is transmitted toward the first direction D1 by the transmission unit 2. Then, the second ultrasonic beam propagates through the subject S with a predetermined spread after converging on the second transmission focus F2.

In this case, a transmission wave toward the reflection point C present in the first direction D1 through the second transmission focus F2 from the probe 1 propagates along the same path R0 as the first ultrasonic beam, and a reflected wave from the reflection point C is received by each element of the probe 1. On the other hand, a transmission wave traveling in the second direction D2 perpendicular to the needle N through the second transmission focus F2 from the probe 1 propagates along a path R2, and a reflected wave from the surface of the needle N is received by each element of the probe 1.

By sequentially transmitting the first ultrasonic beam and the second ultrasonic beam for each scanning line as described above while moving the scanning line in the arrangement direction of the elements of the probe 1, first element data and second element data are generated by the reception unit 3.

Figure 4A:
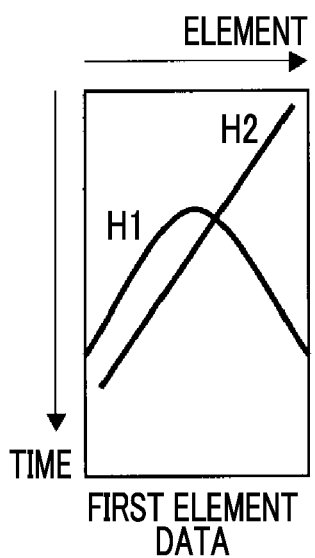
FIGS. 4A-4C are diagrams schematically showing first element data, second element data, and reflection component removal data that are obtained in the first embodiment, respectively.
Figure 4B:
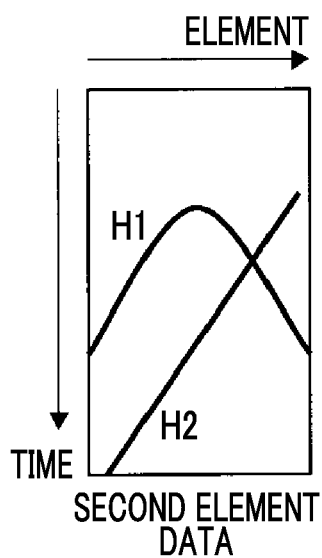

FIGS. 4(A) and 4(B) show the first element data acquired by transmission of the first ultrasonic beam and the second element data acquired by transmission of the second ultrasonic beam, respectively. A reflected wave H1 from the first direction D1 and a reflected wave H2 from the needle N are included in the first element data. Similarly, the reflected wave H1 from the first direction D1 and the reflected wave H2 from the needle N are included in the second element data.

Here, for the reflection point C present in the first direction D1, since the ultrasonic wave propagates by the same propagation length along the same path R0 both when transmitting and receiving the first ultrasonic beam and when transmitting and receiving the second ultrasonic beam, the reflected wave H1 from the first direction D1 is present at the same time position (depth position) in the first element data and the second element data.

On the other hand, for the needle N, when transmitting and receiving the first ultrasonic beam and when transmitting and receiving the second ultrasonic beam, the paths R1 and R2 of the transmission wave are different and the paths of the reflected wave are different. Accordingly, the reflected wave H2 from the needle N is present at different time positions (depth positions) in the first element data and the second element data.

Figure 4C:
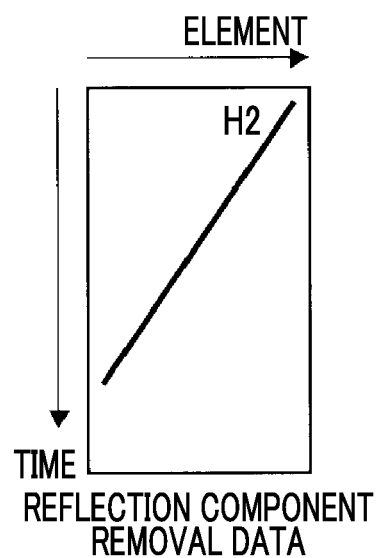

Therefore, it is possible to remove the reflected wave H1 from the first direction D1 while leaving the reflected wave H2 from the needle N by taking the difference between the first element data and the second element data by the difference calculation section 41 that forms the element data processing unit 6. In this case, both the reflected wave H2 from the needle N in the first element data and the reflected wave H2 from the needle N in the second element data are left. However, for example, by removing the reflected wave H2 from the needle N in the second element data, reflection component removal data including the reflected wave H2 from the needle N is generated as shown in FIG. 4(C). Alternatively, it is also possible to generate reflection component removal data by combining the reflected wave H2 from the needle N in the first element data and the reflected wave H2 from the needle N in the second element data.

For example, in difference data obtained by taking the difference between the first element data and the second element data, a plurality of straight lines may be extracted by performing Hough conversion. Then, when one straight line and another long straight line parallel to the straight line are found, one of the straight lines may be removed. That is, in the difference data, the difference value of the linear portion to be removed may be replaced with zero. When removing one of the straight lines, it is preferable to leave a side on which a pattern of the similar linear shape is present at the same position of the first element data. Since the first element data and the second element data also include reflected waves from objects other than the needle, it is needless to say that the above-described processing may be performed after performing processing for reducing or smoothing the first element data and the second element data.

By performing reception focusing in the second direction D2 for the reflection component removal data, it is possible to generate a needle image having an excellent S/N ratio without being influenced by the reflected wave H1 from the first direction D1.

As shown in FIG. 3, in the case of a so-called linear type probe in which a plurality of elements of the probe 1 are linearly arrayed, normal directions of the respective elements are parallel to each other. Accordingly, it is preferable to set the first direction D1 to the normal direction. However, in a so-called convex type probe in which a plurality of elements are arrayed in a curved shape, the normal directions of the respective elements are different. In this case, the first direction D1 can be set to the normal direction of each element.

In addition, the second direction D2 does not necessarily need to be set to a direction perpendicular to the needle N, and may be set to a direction toward the needle N rather than the first direction D1, that is, a direction having an angle close to the right angle with respect to the needle N rather than the normal direction of each element.

Figure 5:
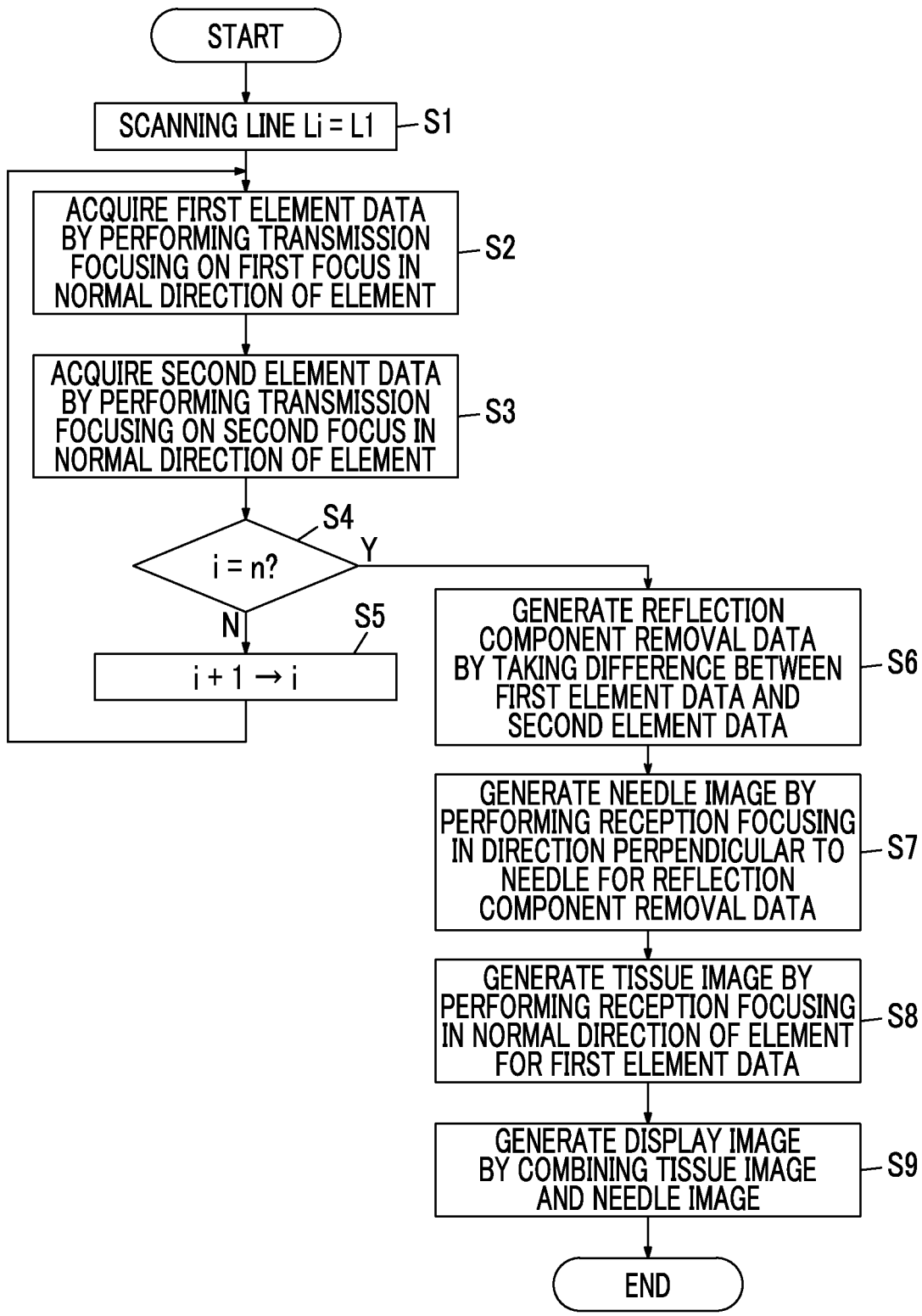
FIG. 5 is a flowchart showing the operation in the first embodiment.

Next, an operation in the first embodiment will be described with reference to the flowchart shown in FIG. 5.

In the first embodiment, it is assumed that a tissue image in the normal direction of the element surface of the probe 1 and a needle image in a direction perpendicular to the needle N are generated by setting n scanning lines L1 to Ln and performing a scan.

First, in step S1, the scanning line L1 is initialized to L1. In step S2, for the first scanning line L1, a reception signal is acquired by performing transmission focusing on the first transmission focus F1 at a predetermined depth in the normal direction of the element surface of the probe 1 that is the first direction D1, and the first element data is acquired by the reception unit 3. That is, according to the driving signal supplied from the transmission unit 2, transmission focusing is performed on the first transmission focus F1 from a plurality of elements that form a transmission opening corresponding to the scanning line L1, and an ultrasonic beam is transmitted. Then, a reception signal output from each element, which is obtained by receiving the reflected wave from the subject, is amplified and digitized by the reception unit 3, and is stored in the element data memory 5.

Then, in step S3, for the same first scanning line, transmission focusing is performed on the second transmission focus F2, which is in the first direction D1 and is at a different depth position from the first transmission focus F1, and second element data is acquired by the reception unit 3 and is stored in the element data memory 5.

Then, in step S4, it is determined whether or not i=n, that is, it is determined whether or not the acquisition of the first element data and the second element data has been completed for all of the n scanning lines L1 to Ln.

Here, since the value of i is still "1", the process proceeds to step S5 to set the value of i to "2" by increasing the value of i by "1", and then the process returns to step S2. Through steps S2 and S3, first element data and second element data corresponding to the second scanning line L2 are acquired, and are stored in the element data memory 5.

Similarly, until i=n, the value of i is increased by 1 in a sequential manner, and steps S2 and S3 are repeated.

When the acquisition of the first element data and the second element data is completed for all of the n scanning lines L1 to Ln as described above, the process proceeds to step S6 from step S4. In step S6, the difference calculation section 41 that forms the element data processing unit 6 calculates a difference between the first element data and the second element data for the scanning lines L1 to Ln stored in the element data memory 5, thereby generating reflection component removal data in which the reflected wave H1 from the first direction D1 has been removed. In this case, in the difference calculation, either the first element data or the second element data or both the first element data and the second element data may be weighted to perform a difference calculation.

Then, in step S7, a needle image is generated by performing reception focusing in a direction perpendicular to the needle N, which is the second direction D2, for the reflection component removal data generated by the difference calculation section 41.

That is, the second reception focusing section 31 of the needle image generation unit 7 generates delay correction data by performing delay correction for the reflection component removal data so that reception focusing is performed in a direction perpendicular to the needle N, and generates a sound ray signal for needle imaging by adding up the pieces of delay correction data. The detection processing section 32 generates a B-mode image signal for needle imaging by performing envelope detection processing on the sound ray signal, and the B-mode image signal for needle imaging is stored in the image memory 33.

In step S8, a tissue image is generated by performing reception focusing in the normal direction of the element surface of the probe 1, which is the first direction D1, for the first element data regarding the scanning lines L1 to Ln stored in the element data memory 5.

That is, the first reception focusing section 21 of the tissue image generation unit 4 generates delay correction data by performing delay correction for each piece of the first element data so that reception focusing is performed in the normal direction of the element surface, and generates a sound ray signal for tissue imaging by adding up the pieces of delay correction data. The detection processing section 22 generates a B-mode image signal for tissue imaging by performing envelope detection processing on the sound ray signal, and the B-mode image signal for tissue imaging is stored in the image memory 23.

Then, in step S9, the B-mode image signal of the tissue image stored in the image memory 23 of the tissue image generation unit 4 and the B-mode image signal of the needle image stored in the image memory 33 of the needle image generation unit 7 are raster-converted by the image combination unit 8, and are combined with each other after various kinds of image processing is performed. As a result, a B-mode image signal of the display image is generated.

The B-mode image signal of the display image is output to the display control unit 9 from the image combination unit 8, and an ultrasonic image in which the tissue image and the needle image are combined is displayed on the display unit 10.

The element data processing unit 6 generates reflection component removal data by removing the reflected wave H1 from the first direction D1, and the second reception focusing section 31 of the needle image generation unit 7 performs reception focusing in the second direction D2 for the reflection component removal data. Therefore, even if the reception focusing is performed in the second direction D2, which is different from the first direction D1 that is the transmission direction of the ultrasonic beam, it is possible to generate a clear needle image having an excellent S/N ratio without being influenced by the reflected wave H1 from the first direction D1.

In the first embodiment described above, the acquisition of the first element data and the second element data is completed for all of the n scanning lines L1 to Ln in steps S1 to S5, and then the reflection component removal data is generated in step S6, and the needle image and the tissue image are generated by performing reception focusing in steps S7 and S8. However, the present invention is not limited thereto. For example, whenever the first element data and the second element data are acquired for each scanning line Li, reflection component removal data corresponding to the scanning line Li may be generated using the first element data and the second element data, and a needle image and a tissue image corresponding to the scanning line L1 may be generated. When a needle image and a tissue image are generated for each of all of the scanning lines L1 to Ln, the needle image and the tissue image are combined.

Second Embodiment

Figure 6:
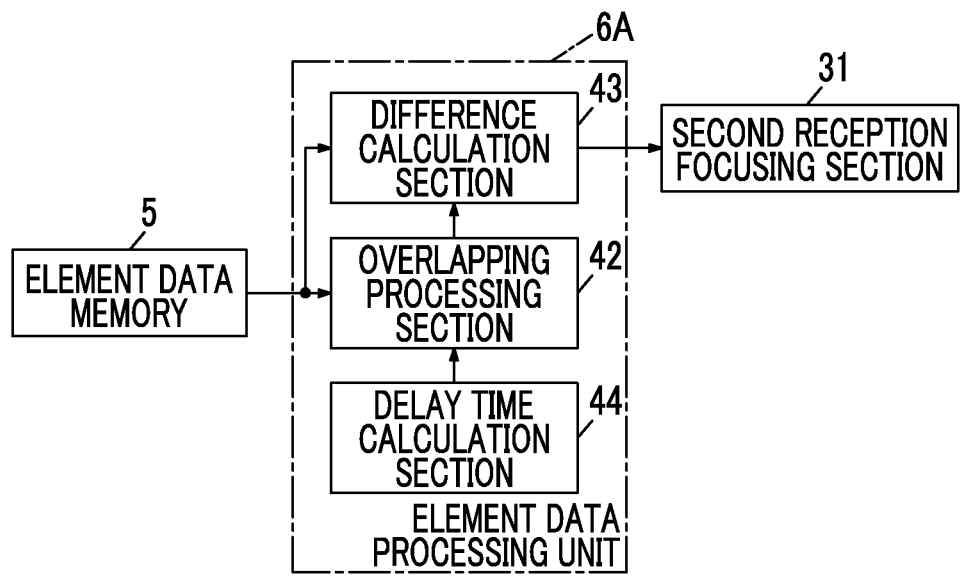
FIG. 6 is a diagram showing the configuration of an element data processing unit in a second embodiment.

FIG. 6 shows the internal configuration of an element data processing unit 6A used in an ultrasonic diagnostic device according to a second embodiment. The ultrasonic diagnostic device has the same configuration as the ultrasonic diagnostic device of the first embodiment shown in FIG. 1 except that the element data processing unit 6A is used instead of the element data processing unit 6.

The element data processing unit 6A includes an overlapping processing section 42 connected to the element data memory 5, and a difference calculation section 43 is connected to both the overlapping processing section 42 and the element data memory 5 and a delay time calculation section 44 is connected to the overlapping processing section 42. The difference calculation section 43 is connected to the second reception focusing section 31 of the needle image generation unit 7.

The overlapping processing section 42 performs overlapping processing for overlapping a predetermined number of pieces of element data, which are generated by the reception unit 3 corresponding to a predetermined number of consecutive elements of the probe 1, with each other by phase matching. The difference calculation section 43 generates reflection component removal data by taking the difference between the overlapping-processed data generated by the overlapping processing section 42 and the element data stored in the element data memory 5.

The delay time calculation section 44 calculates a delay time between the pieces of element data required for the overlapping processing in the overlapping processing section 42.

In the overlapping processing of the overlapping processing section 42, the transmission focus of the ultrasonic beam is regarded as a virtual sound source, a delay difference between the arrival times of reflection points in respective scanning lines is calculated from the geometric propagation length from the sound source to each reflection point, and the signal on each scanning line is emphasized by adding up the pieces of element data of the plurality of scanning lines by correcting the delay difference.

Here, the overlapping processing will be described with reference to FIG. 7.

It is assumed that processing for overlapping three consecutive pieces of element data with each other, among five pieces of element data corresponding to five consecutive scanning lines, is performed.

Figure 7A:
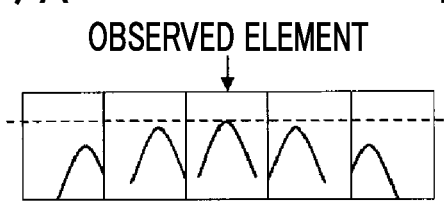
FIG. 7A is a diagram showing five pieces of element data when a central element of a transmission opening is set as a first observed element.

FIG. 7(a) shows a state in which five pieces of element data corresponding to five consecutive scanning lines are displayed side by side and an ultrasonic beam is transmitted and the reflected wave is received. The horizontal axis of each piece of element data indicates an element that receives a reflected wave, and is displayed with a central element of the transmission opening of the ultrasonic beam in each piece of element data at the center. The vertical axis indicates a receiving time.

Among the five pieces of element data, in the central piece of element data, a reflection point is present immediately below the central element of the opening, and the reflected wave from the reflection point is received. That is, the reflected wave is a true signal, and the central element data indicates a true signal.

For the two pieces of element data displayed on both sides of the central piece of element data, no reflection point is present immediately below the central element of the transmission opening. However, due to the spread of the transmitted ultrasonic beam, a reflected wave generated by emitting an ultrasonic beam to the reflection point present immediately below the central element in the central piece of element data, that is, a ghost signal, is reflected. Since the propagation time of the ultrasonic wave to the reflection point increases as a distance from the true signal increases, the receiving time of the ghost signal is delayed from that of the true signal.

In addition, the receiving element that receives the reflected wave from the reflection point first is an element located immediately above the reflection point. However, the horizontal axis of element data is displayed with the central element of the transmission opening of the ultrasonic beam in the corresponding scanning line at the center, and the transmission of an ultrasonic beam is performed by shifting the central element by one element for each scanning line. For this reason, in element data corresponding to each scanning line, the absolute position of the element is shifted by one element. That is, among the five pieces of element data, in the central piece of element data, the receiving element that receives the reflected wave from the reflection point first is an element located at the center. However, in pieces of element data adjacent to both sides of the central piece of element data, the receiving element that receives the reflected wave from the reflection point first is shifted by one element from the central piece of element data. Accordingly, the receiving element that receives the reflected wave from the reflection point first is shifted by one element to the left in the piece of element data adjacent to the right side of the central piece of element data, and is shifted by one element to the right in the piece of element data adjacent to the left side of the central piece of element data. In addition, in pieces of element data located at both ends among the five pieces of element data, the receiving element that receives the reflected wave from the reflection point first is shifted by two elements from the central piece of element data. Accordingly, the receiving element that receives the reflected wave from the reflection point first is shifted by two elements to the left in the piece of element data located at the right end, and is shifted by two elements to the right in the piece of element data located at the left end. Thus, not only is the receiving time of the ghost signal delayed from the receiving time of the true signal, but also the ghost signal differs depending on the arrangement direction of receiving elements.

Figure 7B:
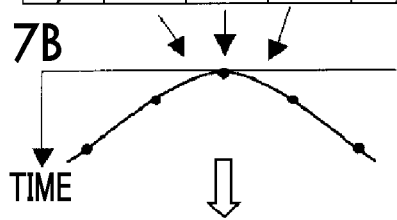
FIG. 7B is a diagram showing a delay time of a receiving time for an element data corresponding to the first observed element.

FIG. 7(b) shows an example of the delay time of the receiving time for the central piece of element data among the five pieces of element data shown in FIG. 7(a).

In the overlapping processing section 42, using the delay time shown in FIG. 7(b), when the central element of the transmission opening is set as an observed element in the central piece of element data among the five pieces of element data, delay time correction is performed by the number of pieces of element data to overlap each other (here, by the delay time corresponding to each of three pieces of element data) with the piece of element data corresponding to the observed element at the center, and the pieces of element data on both sides of the piece of element data corresponding to the observed element are shifted by one element in the horizontal direction so that the absolute position of the central element of the transmission opening in the piece of element data corresponding to the observed element is the same, thereby overlapping the three pieces of element data with each other. That is, the three pieces of element data are made to overlap each other by phase matching. As a result, a piece of overlapping-processed data corresponding to the element data corresponding to the observed element is generated.

The overlapping-processed data obtained as described above is shown in FIG. 7(c).

Figure 7C:
FIG. 7C shows an overlapping-processed data for the element data corresponding to the first observed element.

Among the five pieces of element data shown in FIG. 7(a), the central piece of element data is the element data of a true signal. Therefore, when phase matching is performed by performing delay time correction and horizontal shift for the pieces of element data adjacent to both sides of the central piece of element data, the three pieces of element data overlap each other at a high brightness position as shown in FIG. 7(c). Accordingly, overlapping-processed data having a high brightness value is obtained by adding up the three pieces of element data. In addition, even if an average value is calculated by averaging the three pieces of element data, it is possible to obtain the clear overlapping-processed data in which the brightness is emphasized.

Figure 7D:
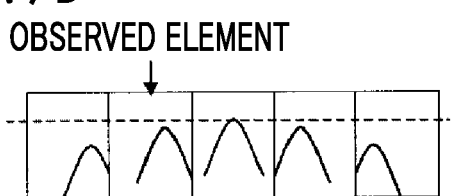
FIG. 7D is a diagram showing five pieces of element data when an element adjacent to the left side of the central element is set as a second observed element.

In contrast, FIG. 7(d) shows an example in which there are five pieces of element data as in FIG. 7(a) but element data adjacent to the left side of the central piece of element data, that is, a central element of the transmission opening corresponding to the ghost signal is set as an observed element.

Figure 7E:
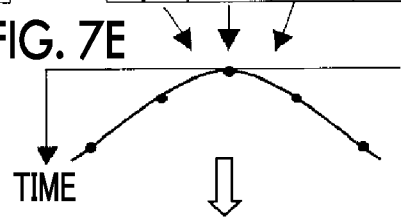
FIG. 7E is a diagram showing a delay time of a receiving time for an element data corresponding to the second observed element.

FIG. 7(e) shows an example of the delay time of the receiving time for the central piece of element data among the five pieces of element data shown in FIG. 7(d), and this is the same as the delay time of the receiving time shown in FIG. 7(b). That is, since the element data in FIG. 7(a) and the element data in FIG. 7(d) are the same, the delay time of the receiving time for the central piece of element data among the five pieces of element data is the same.

In the overlapping processing section 42, using the delay time shown in FIG. 7(e), delay time correction is performed by the number of pieces of element data to overlap each other (here, by the delay time corresponding to each of three pieces of element data) with the piece of element data corresponding to the observed element at the center, and the pieces of element data on both sides of the piece of element data corresponding to the observed element are shifted by one element in the horizontal direction so that the absolute position of the central element of the transmission opening in the piece of element data corresponding to the observed element is the same, thereby overlapping the three pieces of element data with each other. That is, the three pieces of element data are made to overlap each other by phase matching. As a result, a piece of overlapping-processed data corresponding to the element data corresponding to the observed element is generated.

The overlapping-processed data of the element data corresponding to the observed element that has been obtained as described above is shown in FIG. 7(f).

Figure 7F:
FIG. 7F shows an overlapping-processed data for the element data corresponding to the second observed element.

The element data corresponding to the observed element shown in FIG. 7(d) is element data of the ghost signal. Accordingly, even if delay time correction and horizontal shift are performed for element data adjacent to both sides of the element data, three pieces of element data do not overlap each other since the phases do not match each other as shown in FIG. 7(f). For this reason, even if the three pieces of element data are added up, signals having inverted phases or the like are negated since the phases do not match each other. Accordingly, the sum value is not increased. In addition, an average value obtained by averaging the three pieces of element data indicates a small value.

Figure 7G:
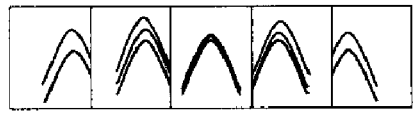
FIG. 7G shows an overlapping state for three consecutive pieces of element data.
Figure 7H:
FIG. 7H shows a result of overlapping processing in the second embodiment.

When the same delay time correction and horizontal shift are performed for five pieces of element data with the central element of the transmission opening as an observed element and three consecutive pieces of element data are made to overlap each other, an overlapping state shown in FIG. 7(g) is obtained. FIG. 7(h) shows a result of, for example, addition processing or averaging processing as overlapping processing that has been performed for these pieces of element data.

As shown in FIG. 7(h), in the central piece of element data indicating the true signal, overlapping-processed data having a high brightness value is generated. In four pieces of element data indicating the ghost signal that are located on both sides of the central piece of element data, the signals are negated since the pieces of element data having phases that do not match each other are added up or averaged. For this reason, the overlapping-processed data corresponding to the four pieces of element data has a smaller value than the overlapping-processed data of the true signal having a high-brightness value at the center.

Accordingly, by performing overlapping processing in the overlapping processing section 42, the influence of the element data of the ghost signal on the element data of the true signal can be negligibly reduced.

In the same manner as in the first embodiment, by forming a transmission focus at a predetermined depth in the first direction D1 that is the normal direction of the element surface of the probe 1, transmitting an ultrasonic beam toward the first direction D1 using the transmission unit 2, and receiving the reflected wave in each element of the probe 1, element data shown in FIG. 8(A) is obtained. The reflected wave H1 from the first direction D1 and the reflected wave H2 from the needle N are included in the element data.

Here, the reflected wave H1 from the first direction D1 can be regarded as a true signal obtained by receiving the reflected wave from the reflection point on each scanning line, and the reflected wave H2 from the needle N can be regarded as a ghost signal that is reflected by the spread of the transmitted ultrasonic beam.

Therefore, by making the overlapping processing section 42 perform overlapping processing for the element data stored in the element data memory 5 so that the influence of the reflected wave H2 from the needle N can be negligibly reduced as shown in FIG. 8(B), it is possible to generate overlapping-processed data in which the reflected wave H1 from the first direction D1 is emphasized.

Therefore, by taking the difference between the element data stored in the element data memory 5 and the overlapping-processed data generated by the overlapping processing section 42 using the difference calculation section 43, reflection component removal data in which the reflected wave H1 from the first direction D1 has been removed while leaving the reflected wave H2 from the needle N is generated as shown in FIG. 8(C).

By performing reception focusing in the second direction D2 for the reflection component removal data, it is possible to generate a needle image having an excellent S/N ratio without being influenced by the reflected wave H1 from the first direction D1.

Figure 9:
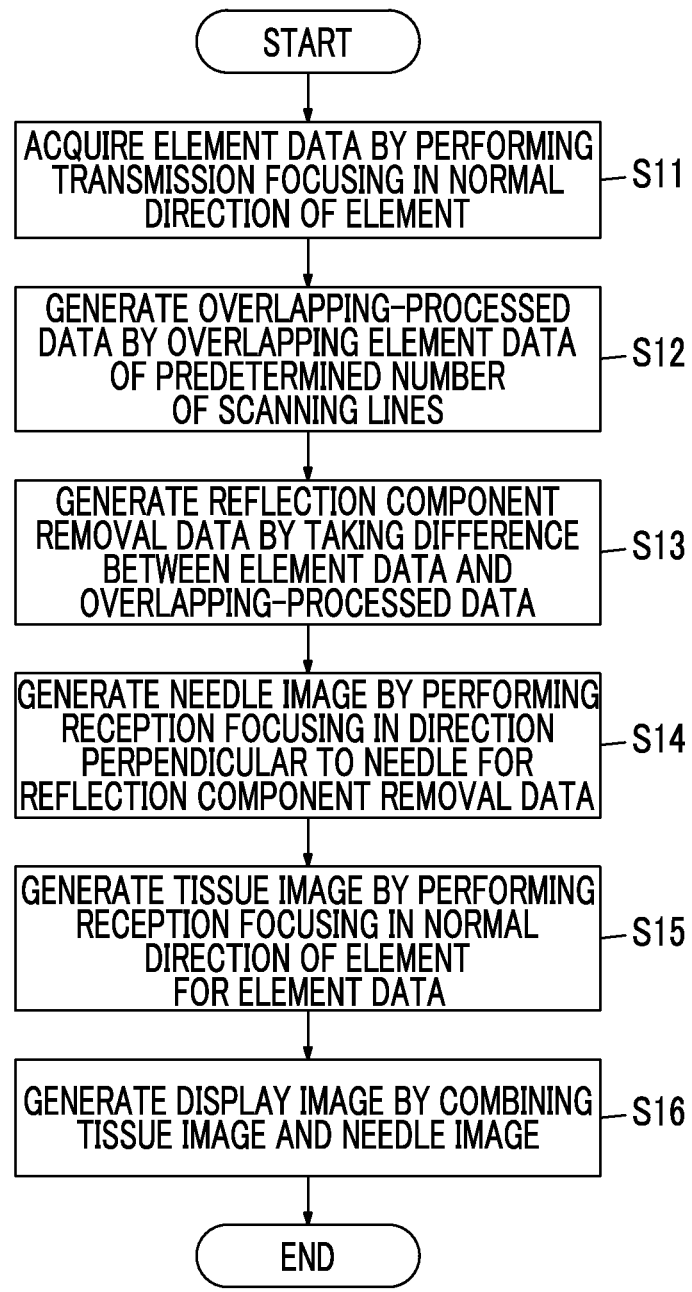
FIG. 9 is a flowchart showing the operation in the second embodiment.

Next, an operation in the second embodiment will be described with reference to the flowchart shown in FIG. 9.

First, in step S11, for each scanning line, transmission focusing is performed on a transmission focus at a predetermined depth in the normal direction of the element surface of the probe 1 that is the first direction D1, thereby acquiring a reception signal. As a result, element data is acquired by the reception unit 3. Similarly, element data for all scanning lines is acquired, and is stored in the element data memory 5.

Then, in step S12, for the element data stored in the element data memory 5, overlapping processing is performed by the overlapping processing section 42 of the element data processing unit 6A. That is, pieces of element data corresponding to a predetermined number of consecutive scanning lines are made to overlap each other by phase matching, so that overlapping-processed data is generated. In this case, by setting the predetermined number of scanning lines, for which pieces of element data are made to overlap each other, to, for example, about 10, it is possible to generate overlapping-processed data in which the reflected wave H2 from the needle N is not emphasized while emphasizing the reflected wave H1 generated from the first direction D1.

In addition, the delay time between the pieces of element data required for overlapping processing is calculated by the delay time calculation section 44 of the element data processing unit 6A.

Then, in step S13, a difference between the element data stored in the element data memory 5 and the overlapping-processed data generated by the overlapping processing section 42 is generated by the difference calculation section 43 of the element data processing unit 6A, so that reflection component removal data in which the reflected wave H1 from the first direction D1 has been removed while leaving the reflected wave H2 from the needle N is generated.

In this case, the difference calculation section 43 may calculate the difference after giving a weighting to either the element data stored in the element data memory 5 or the overlapping-processed data generated by the overlapping processing section 42 or to both the element data stored in the element data memory 5 and the overlapping-processed data generated by the overlapping processing section 42. In addition, it is also possible to change the value of the weighting and the calculation method depending on the depth.

Then, in step S14, the needle image generation unit 7 generates a B-mode image signal for needle imaging by performing reception focusing in a direction perpendicular to the needle N, which is the second direction D2, for the reflection component removal data generated by the difference calculation section 43, and the B-mode image signal for needle images is stored in the image memory 33.

Then, in step S15, the tissue image generation unit 4 generates a B-mode image signal for tissue imaging by performing reception focusing in the normal direction of the element surface of the probe 1, which is the first direction D1, for the element data stored in the element data memory 5, and the B-mode image signal for tissue images is stored in the image memory 23.

Then, in step S16, the B-mode image signal of the tissue image stored in the image memory 23 of the tissue image generation unit 4 and the B-mode image signal of the needle image stored in the image memory 33 of the needle image generation unit 7 are raster-converted by the image combination unit 8, and are combined with each other after various kinds of image processing are performed. As a result, a B-mode image signal of the display image is generated.

The B-mode image signal of the display image is output to the display control unit 9 from the image combination unit 8, and an ultrasonic image in which the tissue image and the needle image are combined is displayed on the display unit 10.

The overlapping-processed data in which the reflected wave H1 generated from the first direction D1 is emphasized is generated by the overlapping processing section 42 of the element data processing unit 6A, the reflection component removal data in which the reflected wave H1 from the first direction D1 has been removed is generated by the difference calculation section 43, and reception focusing is performed in the second direction D2 for the reflection component removal data by the second reception focusing section 31 of the needle image generation unit 7. Therefore, even if the reception focusing is performed in the second direction D2 different from the first direction D1 that is the transmission direction of the ultrasonic beam, it is possible to generate a clear needle image with an excellent S/N ratio without being influenced by the reflected wave H1 from the first direction D1.

In the second embodiment described above, the tissue image generation unit 4 generates a B-mode image signal for tissue imaging by performing reception focusing in the first direction D1 for the element data stored in the element data memory 5. However, the present invention is not limited thereto. For example, the tissue image generation unit 4 may be configured to generate a B-mode image signal for tissue imaging by performing reception focusing in the first direction D1 for the overlapping-processed data which is generated by the overlapping processing section 42 of the element data processing unit 6A and in which the reflected wave H1 generated from the first direction D1 is emphasized.

In step S12, a predetermined number of consecutive scanning lines are set as scanning lines to be subjected to overlapping processing by the overlapping processing section 42 of the element data processing unit 6A. However, the scanning lines to be subjected to overlapping processing by the overlapping processing section 42 of the element data processing unit 6A do not necessarily need to be consecutive, or may not be consecutive as long as these are scanning lines in a range where pieces of element data overlap each other.

Third Embodiment

Figure 10:
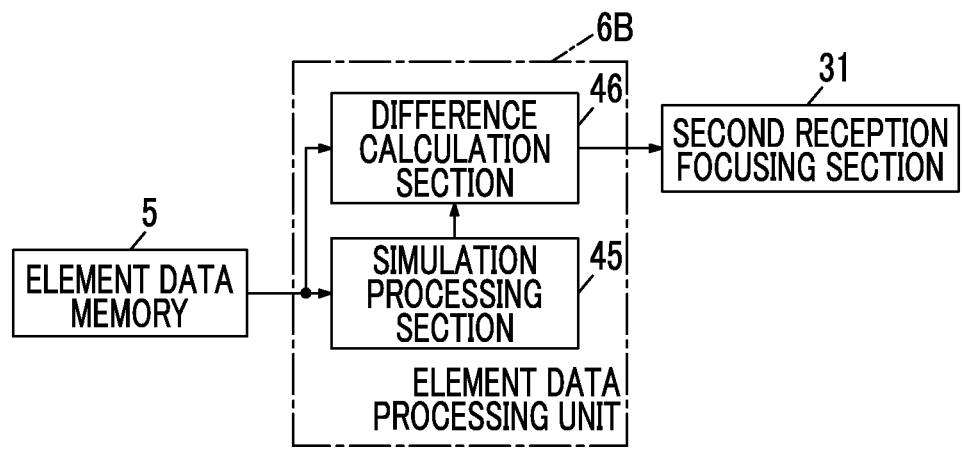
FIG. 10 is a diagram showing the configuration of an element data processing unit in a third embodiment.

FIG. 10 shows the internal configuration of an element data processing unit 6B used in an ultrasonic diagnostic device according to a third embodiment. The ultrasonic diagnostic device has the same configuration as the ultrasonic diagnostic device of the first embodiment shown in FIG. 1 except that the element data processing unit 6B is used instead of the element data processing unit 6.

The element data processing unit 6B includes a simulation processing section 45 connected to the element data memory 5. A difference calculation section 46 is connected to the simulation processing section 45, and the difference calculation section 46 is connected to the second reception focusing section 31 of the needle image generation unit 7.

The simulation processing section 45 generates simulation data indicating the reflected wave H1 generated from the first direction D1 by performing simulation processing, and the difference calculation section 46 generates reflection component removal data by taking the difference between the simulation data generated by the simulation processing section 45 and the element data stored in the element data memory 5.

Figure 11:
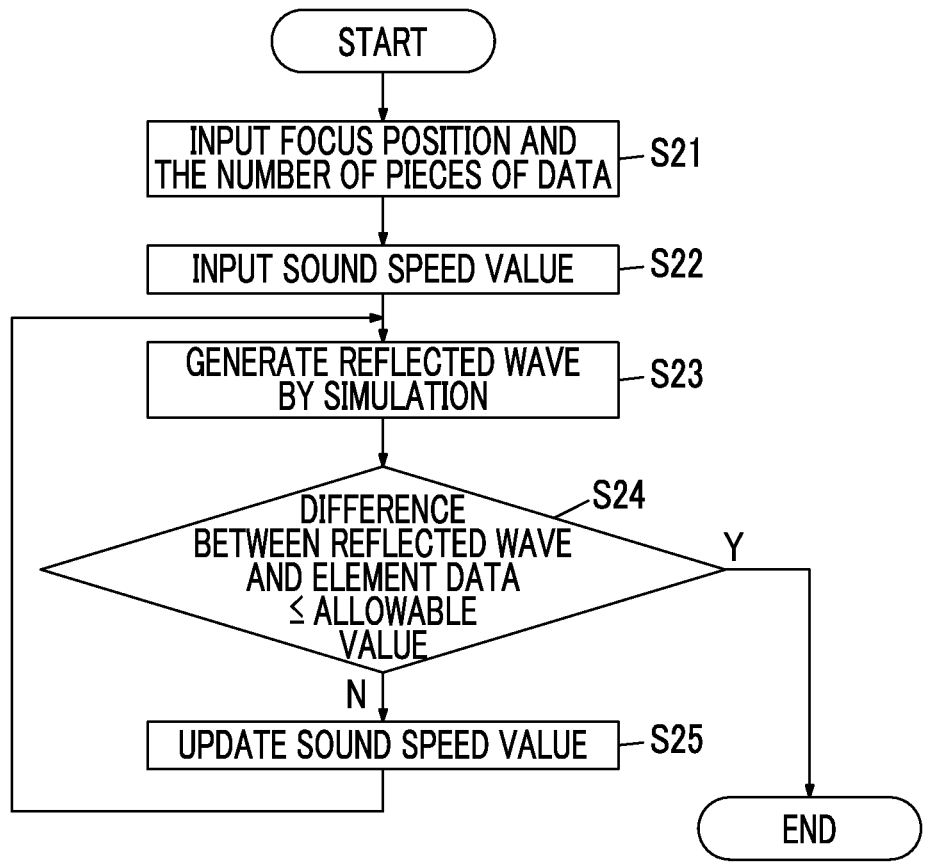
FIG. 11 is a flowchart showing the operation of simulation processing in the third embodiment.

The simulation processing in the simulation processing section 45 is for generating the reflected wave from the reflection point located on each scanning line by simulation, and the operation is shown in the flowchart of FIG. 11.

In addition, it is assumed that element data is acquired in advance by actually transmitting and receiving ultrasonic beams in the ultrasonic diagnostic device of the third embodiment.

In step S21, measurement conditions when actually acquiring element data, such as a focus position and the number of pieces of data, is input.

Then, in step S22, a sound speed value required for the operation of simulation is input.

Then, in step S23, the operation of simulation is executed using the measurement conditions input in step S21 and the sound speed value input in step S22, thereby generating a reflected wave.

After the reflected wave is generated as described above, in subsequent step S24, a difference between the generated reflected wave and the element data acquired in advance by actually transmitting and receiving ultrasonic beams is calculated, and it is determined whether or not the difference is equal to or less than the allowable value set in advance.

When it is determined that the difference exceeds the allowable value in step S24, the process proceeds to step S25 to update the sound speed value to a new value. Then, the process returns to step S23 in which a reflected wave is generated by performing simulation again using the updated sound speed value. Then, in step S24, a difference between the new reflected wave and the element data acquired in advance is calculated, and it is determined whether or not the difference is equal to or less than the allowable value.

Since the shape of the reflected wave generated by the simulation changes according to the sound speed value to be used, steps S23 to S25 are repeated while updating the sound speed value until the difference between the reflected wave and the element data becomes within the allowable value.

When it is determined that the difference between the reflected wave and the element data becomes within the allowable value in step S24, the reflected wave at this time is set as simulation data generated by the simulation processing, and the simulation processing is ended.

As the sound speed value, it is possible to generate a reflected wave by simulation by inputting a fixed value that does not depend on the depth. Alternatively, a reflected wave by simulation may be generated for each depth by inputting a different sound speed value for each depth.

Figure 12A:
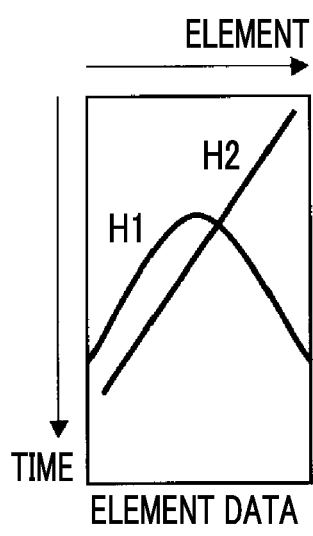
FIGS. 12A-12C are diagrams schematically showing element data, simulation data, and reflection component removal data that are obtained in the third embodiment, respectively.

In the same manner as in the first embodiment, by forming a transmission focus at a predetermined depth in the first direction D1 that is the normal direction of the element surface of the probe 1, transmitting an ultrasonic beam toward the first direction D1 using the transmission unit 2, and receiving the reflected wave in each element of the probe 1, element data shown in FIG. 12(A) is obtained. The reflected wave H1 from the first direction D1 and the reflected wave H2 from the needle N are included in the element data.

Figure 12B:
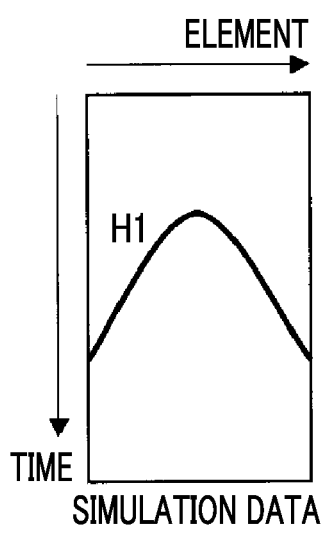

Since the simulation processing in the simulation processing section 45 is for generating the reflected wave from the reflection point located on each scanning line by simulation, simulation data including the reflected wave H1 from the first direction D1 can be generated as shown in FIG. 12(B) by performing simulation processing.

Figure 12C:
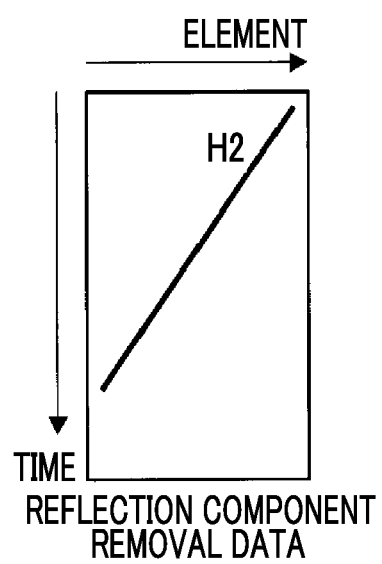

Therefore, by taking the difference between the element data stored in the element data memory 5 and the simulation data generated by the simulation processing section 45 using the difference calculation section 46, reflection component removal data in which the reflected wave H1 from the first direction D1 has been removed while leaving the reflected wave H2 from the needle N is generated as shown in FIG. 12(C).

By performing reception focusing in the second direction D2 for the reflection component removal data, it is possible to generate a needle image having an excellent S/N ratio without being influenced by the reflected wave H1 from the first direction D1.

Figure 13:
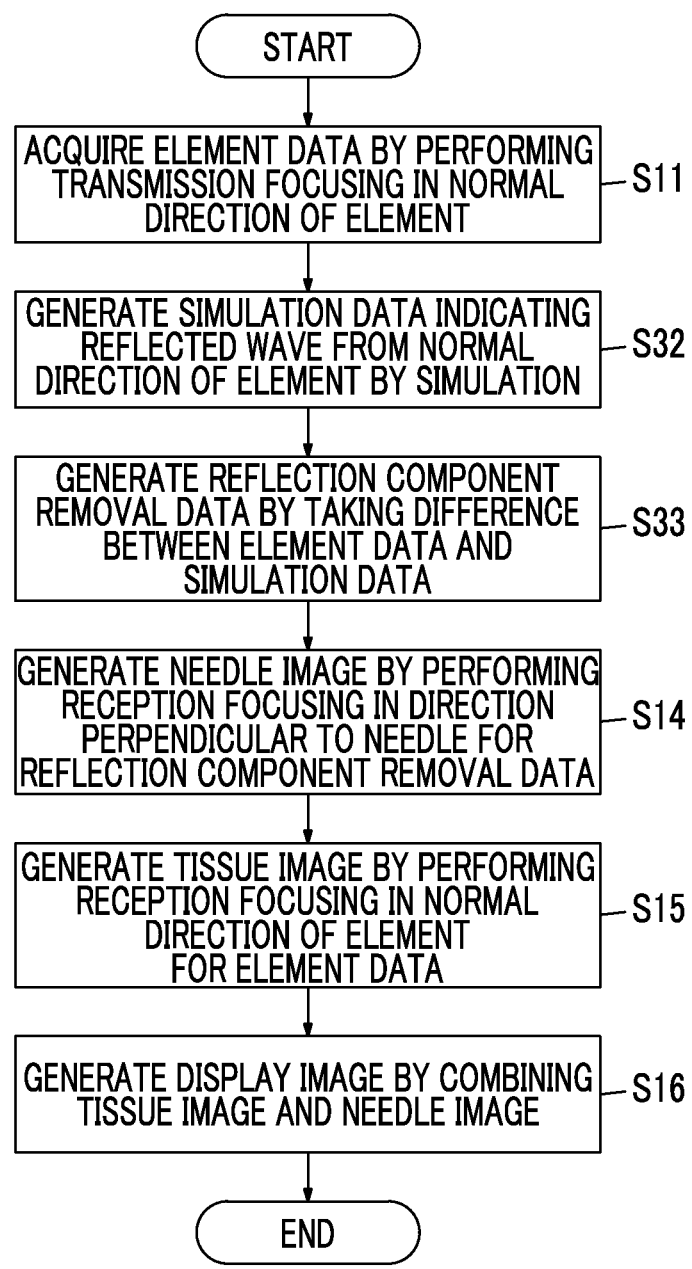
FIG. 13 is a flowchart showing the operation in the third embodiment.

Next, an operation in the third embodiment will be described with reference to the flowchart shown in FIG. 13. In the flowchart shown in FIG. 13, steps S32 and S33 are executed instead of steps S12 and S13 in the flowchart of the second embodiment shown in FIG. 9, and other steps are the same as those in the flowchart shown in FIG. 9.

First, in step S11, for each scanning line, transmission focusing is performed on a transmission focus at a predetermined depth in the normal direction of the element surface of the probe 1 that is the first direction D1, thereby acquiring a reception signal. As a result, element data is acquired by the reception unit 3. Similarly, element data for all scanning lines is acquired, and is stored in the element data memory 5.

Then, in step S32, simulation data indicating the reflected wave H1 generated from the first direction D1 is generated by the simulation processing section 45 of the element data processing unit 6B.

Then, in step S33, a difference between the element data stored in the element data memory 5 and the simulation data generated by the simulation processing section 45 is generated by the difference calculation section 46 of the element data processing unit 6B, so that reflection component removal data in which the reflected wave H1 from the first direction D1 has been removed while leaving the reflected wave H2 from the needle N is generated. In this case, in the difference calculation, either the element data or the simulation data or both the element data and the simulation data may be weighted to perform a difference calculation.

Then, in step S14, the needle image generation unit 7 generates a B-mode image signal for needle imaging by performing reception focusing in a direction perpendicular to the needle N, which is the second direction D2, for the reflection component removal data generated by the difference calculation section 46, and the B-mode image signal for needle images is stored in the image memory 33.

Then, in step S15, the tissue image generation unit 4 generates a B-mode image signal for tissue imaging by performing reception focusing in the normal direction of the element surface of the probe 1, which is the first direction D1, for the element data stored in the element data memory 5, and the B-mode image signal for tissue images is stored in the image memory 23.

Then, in step S16, the B-mode image signal of the tissue image stored in the image memory 23 of the tissue image generation unit 4 and the B-mode image signal of the needle image stored in the image memory 33 of the needle image generation unit 7 are raster-converted by the image combination unit 8, and are combined with each other after various kinds of image processing are performed. As a result, a B-mode image signal of the display image is generated.

The B-mode image signal of the display image is output to the display control unit 9 from the image combination unit 8, and an ultrasonic image in which the tissue image and the needle image are combined is displayed on the display unit 10.

The simulation data indicating the reflected wave H1 generated from the first direction D1 is generated by the simulation processing section 45 of the element data processing unit 6B, the reflection component removal data in which the reflected wave H1 from the first direction D1 has been removed is generated by the difference calculation section 46, and reception focusing is performed in the second direction D2 for the reflection component removal data by the second reception focusing section 31 of the needle image generation unit 7. Therefore, even if the reception focusing is performed in the second direction D2 different from the first direction D1 that is the transmission direction of the ultrasonic beam, it is possible to generate a clear needle image with an excellent S/N ratio without being influenced by the reflected wave H1 from the first direction D1.

Although the B-mode image signal of the tissue image and the B-mode image signal of the needle image are combined by the image combination unit 8 and the result is displayed on the display unit 10 in the first to third embodiments described above, reflection component removal data obtained by removing the reflected wave H1 from the first direction D1 may be combined with the B-mode image, which is a tissue image, as it is and the result is displayed.

The needle image can be displayed in various kinds of display formats, such as a binary image and color display.

In addition, only the needle image may be displayed on the display unit 10 without combining the needle image with the tissue image. Also in this case, it is possible to use various kinds of display formats, such as a B-mode image, reflection component removal data itself, a binary image, and color display.

EXPLANATION OF REFERENCES

1: probe
2: transmission unit
3: reception unit
4: tissue image generation unit
5: element data memory
6, 6A, 6B: element data processing unit
7: needle image generation unit
8: image combination unit
9: display control unit
10: display unit
11: control unit
12: operation unit
13: storage unit
21: first reception focusing section
22, 32: detection processing section
23, 33: image memory
31: second reception focusing section
41, 43, 46: difference calculation section
42: overlapping processing section
44: delay time calculation section
45: simulation processing section
D1: first direction
D2: second direction
F1: first transmission focus
F2: second transmission focus
C: reflection point
R0, R1, R2: path
RA: reception opening
T: element located at center
N: needle
θ: insertion angle
S: subject

What is claimed is:

1. An ultrasonic diagnostic device, comprising:
a probe including a plurality of elements that are arranged;
a transmission circuit that includes a plurality of pulse generators and forms at least two focuses at different depths in a first direction to sequentially transmit a plurality of ultrasonic beams from the plurality of elements of the probe by performing transmission focusing in the first direction,
wherein one beam of the plurality of ultrasonic beams is transmitted by performing transmission focusing on a first focus and another beam of the plurality of ultrasonic beams is transmitted by performing transmission focusing on a second focus;
a reception signal processor that generates a plurality of pieces of element data corresponding to the plurality of ultrasonic beams by processing reception signals output from the plurality of elements of the probe that have received ultrasonic echoes generated by the plurality of ultrasonic beams transmitted from the plurality of elements of the probe;
a central processing unit (CPU); and
an operation program causing the CPU
to take a difference between intensities of a first element data and a second element data among the plurality of pieces of element data to generate reflection component removal data by removing a reflection component generated from the first direction from the plurality of pieces of element data,
wherein the first element data is generated correspondingly to the one beam transmitted by performing transmission focusing on the first focus and the second element data is generated correspondingly to the another beam transmitted by performing transmission focusing on the second focus; and
to perform reception focusing in a second direction different from the first direction for the reflection component removal data to generate an image signal along the second direction.

2. The ultrasonic diagnostic device according to claim 1, wherein, when taking the difference between the intensities of the first element data and the second element data, the CPU takes the difference after giving weighting to either the first element data or the second element data or both the first element data and the second element data.

3. The ultrasonic diagnostic device according to claim 1, wherein the CPU generates an image signal for tissue imaging along the first direction by performing reception focusing in the first direction for the element data and an image signal for needle imaging along the second direction by performing the reception focusing in the second direction for the reflection component removal data.

4. The ultrasonic diagnostic device according to claim 3, wherein the CPU combines the image signal for tissue imaging and the image signal for needle imaging to generate the image signal along the second direction.

5. The ultrasonic diagnostic device according to claim 4, further comprising: a display that displays an ultrasonic image based on the image signal for tissue imagining and the image signal for needle imaging obtained by the CPU.

6. The ultrasonic diagnostic device according to claim 1, further comprising:
a display that displays an ultrasonic image based on the image signal obtained by the CPU.

7. An ultrasonic image generation method, comprising:
forming at least two focuses at different depths in a first direction to sequentially transmit a plurality of ultrasonic beams from a plurality of elements of a probe by performing transmission focusing in the first direction, wherein one beam of the plurality of ultrasonic beams is transmitted by performing transmission focusing on a first focus and another beam of the plurality of ultrasonic beams is transmitted by performing transmission focusing on a second focus;

generating a plurality of pieces of element data corresponding to the plurality of ultrasonic beams by processing reception signals output from the plurality of elements of the probe that has received ultrasonic echoes generated by the plurality of ultrasonic beams transmitted from the plurality of elements of the probe;

taking a difference between intensities of a first element data and a second element data among the plurality of pieces of element data to generate reflection component removal data by removing a reflection component generated from the first direction from the plurality of pieces of element data,
wherein the first element data is generated correspondingly to the one beam transmitted by performing transmission focusing on the first focus and the second element data is generated correspondinginly to the another beam transmitted by performing transmission focusing on the second focus; and performing reception focusing in a second direction different from the first direction for the reflection component removal data to generate an image signal along the second direction.

\* \* \* \* \*